United States Patent [19]

Yoshida et al.

[11] Patent Number: 4,646,333

[45] Date of Patent: Feb. 24, 1987

[54] CT SCANNER

[75] Inventors: Tadatoki Yoshida, Ootawara; Kouji Natori, Tochigi, both of Japan

[73] Assignee: Kabushiki Kaisha Toshiba, Kawasaki, Japan

[21] Appl. No.: 635,205

[22] Filed: Jul. 27, 1984

[30] Foreign Application Priority Data

Jul. 29, 1983 [JP] Japan .................................. 58-137601

[51] Int. Cl.⁴ ............................................. H05G 1/06
[52] U.S. Cl. ......................................... 378/4; 378/15; 378/194
[58] Field of Search ........................... 378/15, 4, 194; 174/117 F

[56] References Cited

U.S. PATENT DOCUMENTS 3,082,292 3/1963 Gore ................................ 174/117 F
4,366,577 12/1982 Brandt ................................ 378/194
4,368,535 1/1983 Baumann ............................. 378/15

FOREIGN PATENT DOCUMENTS 57-177275 10/1982 Japan .

Primary Examiner—Bruce C. Anderson
Assistant Examiner—Jack I. Berman
Attorney, Agent, or Firm—Finnegan, Henderson, Farabow, Garrett & Dunner

[57] ABSTRACT

An X-ray CT scanner contains a cable-handling device provided with a ring-shaped housing for receiving a cable member. A plurality of rollers are interposed between a rotatable inner peripheral and a fixed outer peripheral member of the ring-shaped housing. The cable member is wound around the inner peripheral member at least once, then wound about half the periphery of a specified roller, and finally wound around the outside of the group of the rollers in a direction opposite to that in which the cable member is wound within the housing. The end portions of the cable member facing the inner and outer peripheral members of the housing are fixed thereto. Mounted on a rotating frame are an X-ray tube, X-ray detector and high voltage generator. The high voltage generator and X-ray tube are connected together by a short high voltage cable. The inner peripheral member is rotated with the rotating frame. The cable member is wound around the inner peripheral member or unwound therefrom. The rollers are provided between the cable member wound around the inner peripheral member and the cable member wound around the outside of the group of rollers. The rollers are driven with the rotation of the inner peripheral member of the housing, thereby preventing the cable member from being displaced from the regular rotation course.

8 Claims, 7 Drawing Figures

F I G. 2
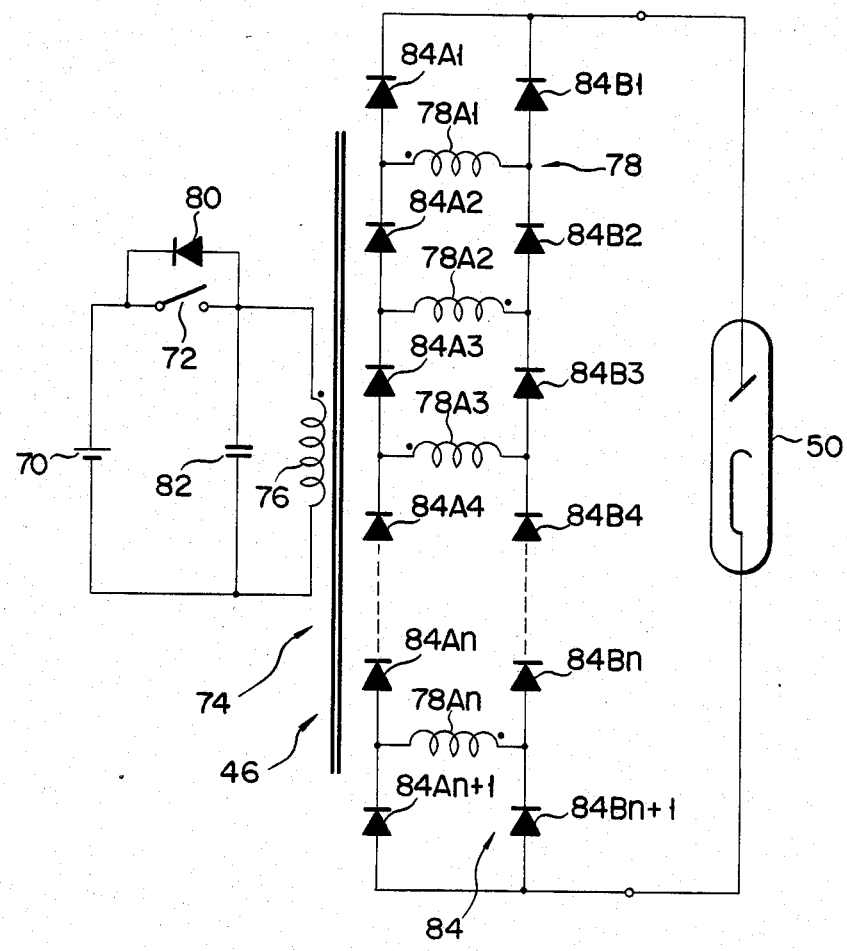

CT SCANNER

BACKGROUND OF THE INVENTION

This invention relates to a computed tomography (hereafter abbreviated as "CT") scanner provided with a continuously rotatable frame on which a radiation tube is mounted.

With the conventional X-ray CT scanner, an X-ray tube is fitted with a rotating frame having a larger diameter than a hole into which a patient is inserted. A high voltage slip ring is interposed between the rotating frame and fixed X-ray CT scanner body. The surrounding region of the high voltage slip ring is sealed by an insulating gas introduced by a seal member. The slip ring is connected at one end to an X-ray tube and at the other end to a large, heavy high voltage generator built on the floor. The rotating frame is freely rotated, while the high voltage generator supplies high voltage to the X-ray tube.

When, however, the rotating frame is turned at a high speed of 30~60 RPM, heat is built up in the seal member due to abrasion, noticeably deteriorating its performance and leading to its wear in a short length of time. Further, arcs arising between the stator and brush of the slip ring result in the denaturalization of the insulating gas and the evolution of noxious and malodorous gases. These gases also reduce the performance of the seal member. The slip ring impressed with high voltage is subject to abrasion and damage due to dust being produced by the brush. Since the deterioration of the seal member leads to the leakage of the insulating gas, it is necessary to frequently perform maintenance an the slip ring and, where necessary, exchange a damaged slip ring for a fresh one.

To attempt to resolve the above-mentioned difficulties, a high voltage generator can be fitted to the rotating frame on which the X-ray tube is mounted, and a low voltage slip ring mounted on the rotating frame. If, however, an X-ray tube including an oil cooler which measures 30 to 60 kg and a high voltage generator weighing, for example, 800 to 1,160 kg is mounted on the rotating frame, difficulties will occur in smoothly driving the rotating frame. Further, the ordinary rotating frame requires a sufficiently large space for the mounting of a large high voltage generator. Even if impressed with low voltage, the slip ring tends to be abraded and has to be frequently maintained.

If it is attempted to rotate the rotating frame without the slip ring, a long high voltage cable has to be interposed between a high voltage generator built on the floor and an X-ray tube. If a long high voltage cable is applied in this case, tailing appears in the high voltage pulses impressed on the X-ray tube. Thus, a pulse period ending with the fading out of the tailing is extended. As a result, contraction takes place in the timing for the collection of data, ADC and the transmission of data. If attempts are made to stop the collection of data during the appearance of the tailing, then exposing of unnecessary X-rays to the patient continues all the same, thereby exerting a harmful effect on the patient being examined.

SUMMARY OF THE INVENTION

It is accordingly the object of this invention to provide an X-ray CT scanner which can impress tailing-free X-ray pulses on an X-ray tube and drive an X-ray tube-carrying rotating frame with a prescribed frequency without providing a slip ring.

To attain the above-mentioned object, this invention provides a CT scanner for producing transverse layer images of a patient comprising a rotating frame which has a hole, permitting the insertion of the patient, and can turn around the hole, a radiation source which is mounted on the rotating frame to expose fan shaped radiation beams on the patient, a radiation detector which is set on the rotating frame to detect the radiation beams permeating the patient, a high voltage generator which is built on the rotating frame to impress a high voltage on the radiation source, a power source securely set in place, a cable member for effecting the connection between the power source and high voltage generator, and a cable-handling device for holding the cable member so as to permit the rotation of the rotating frame, the cable-handling device comprising a ring-shaped housing which is provided with an outer peripheral member and an inner peripheral member and is intended to hold a cable member wound between the outer peripheral member and inner peripheral member, either of which is made rotatable and the other of which is fixed, and further comprising a plurality of rollers which are arranged in the housing in its circumferential direction with the rotating axis of said rollers aligned with that of the rotating frame, and the cable-handling device being further characterized in that the cable member is wound around the inner peripheral member of the ring-shaped housing at least once in a first direction, wound about half the periphery of the prescribed one of the plural rollers, and wound at least once around the outside of the group of rollers in a second direction opposite to the first direction, and the end portions of the cable member facing the outer and inner peripheral members are fixed thereto.

An X-ray CT scanner embodying this invention which dispenses with a slip ring is saved from the wear and damage of the stator and brush, the deterioration of the seal member and the leakage of insulating gas, and makes it unnecessary to maintain the slip ring and exchange a defective slip ring for a fresh one. Even when the rotating frame is turned at an optional speed, the cable member is smoothly handled by the cable-handling device. With the subject CT scanner, a small, light-weight high voltage generator is mounted on the rotating frame, making it possible to apply an extremely short high voltage cable. Consequently, data can be collected in a short time, and the reduction of the timing of ADC and data transmission is prevented.

With the CT scanner of this invention, it is possible to eliminate the dead time of a cardiac scan intended for the diagnosis of heart problems. In the case of the dynamic scan of, for example, the liver and cerebrum, the dead time is eliminated, and rapid changes in the CT value after the infusion of an opaque substance can be fully followed, thereby elevating the effect of a clinical treatment.

Further, a ring-shaped coupling member is provided which extends along the periphery of the housing. This coupling member causes the shafts of the plural rollers arranged around the periphery of the housing to be fixed in place at a prescribed distance from each other. Therefore, the plural rollers are prevented from being gathered in a single spot within the housing, enabling the cable member to be handled more smoothly.

BRIEF DESCRIPTION OF THE DRAWINGS

FIG. 2 is a circuit diagram of a high voltage generator;

DETAILED DESCRIPTION OF THE PREFERRED EMBODIMENT

Figure 1:
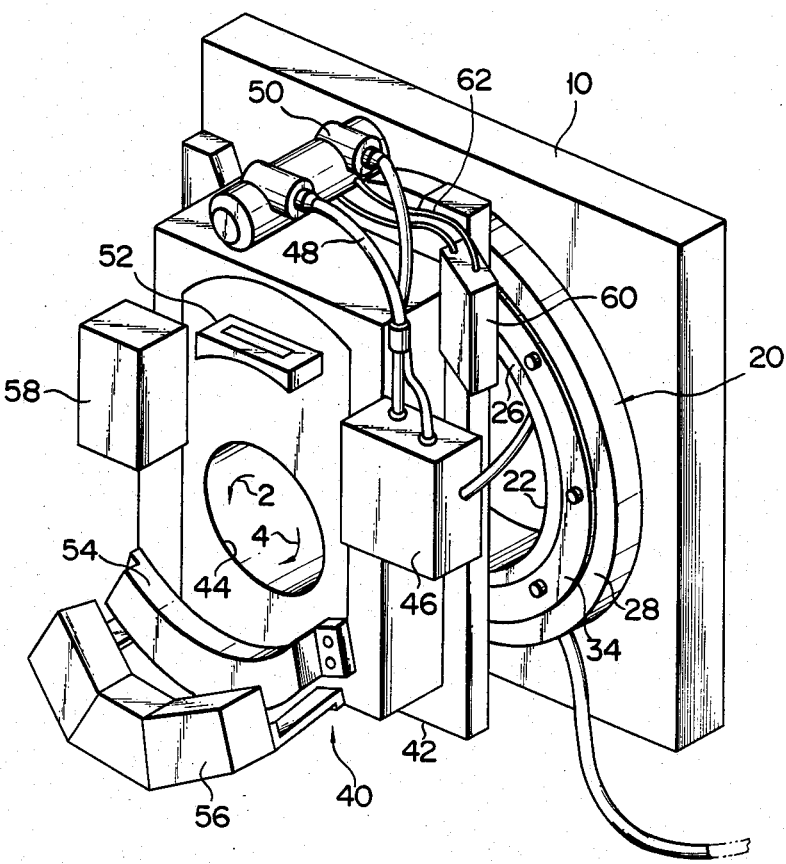
FIG. 1 is an external oblique view of an X-ray CT scanner embodying this invention.

FIG. 1 is an external oblique view of an X-ray CT scanner embodying this invention. A cable-handling device 20 is mounted on a frame 10 of an X-ray CT scanner body. The cable-handling device 20 is a ring-shaped flat board. A hole 22 is provided in the center of the cable-handling device 20 to allow for the insertion of a patient (not shown). A rotating frame 40 is set near the cable-handling device 20. A hole 44 is made in the center of the rotating frame 40 to allow for the insertion of the patient. The rotating frame 40 is rotatably supported by a proper support means (not shown), while the hole 44 is aligned with the hole 22 and is rotated in both directions by a drive means (not shown).

The rotating frame 40 has a support body 42, on which a power supply device 58 and high voltage generator 46 are mounted. An X-ray iris diaphragm 52 and an X-ray detector 54 are fitted to the support body 42 on the opposite sides of the patient inserting hole 44.

An X-ray tube 50 is set near the X-ray iris diaphragm 52. This X-ray tube 50 is connected to the high voltage generator 46 by a short high voltage cable 48. The X-ray tube emits fan shaped X-ray beams upon receiving high voltage from the high voltage generator 46. Fan shaped X-ray beams from the X-ray tube 50 are irradiated on the patient placed in the inserting hole 44 while being properly throttled by the iris diaphragm 52. X-rays passing through an X-ray emission region, defined by the iris diaphragm 52, are detected by the X-ray detector 54. Data supplied from the X-ray detector 54 are collected in a data acquisition system 56.

The X-ray detector 54 and data acquisition system 56 receive power from a power source 58. An oil cooler 60 is connected to the X-ray tube 50 by means of a tube 62. Cool oil, delivered from the oil cooler 60, is circulated through the X-ray tube 50 for cooling.

The high voltage generator 46 may be provided by a resonance DC-DC converter-type high voltage generator set forth, for example, in the Japanese Patent Disclosures 82-177,273, 82-177,274 and 82-177,275, Nikkei Electronics (Oct. 12, 1981) pp. 213-236 and a collection of lectures (p. 542) delivered in the 1981 national convention of the Electrocommunication Society. A high voltage generator of the abovementioned type is small and light and does not obstruct the rotational balance of the rotating frame 40 when mounted on its support 42.

In FIG. 2 is a circuit diagram of the high voltage generator 46 set forth in the Japanese Patent Disclosure No. 82-177,273. Reference numeral 70 is a DC source installed, for example, on the floor. This DC source 70 and high voltage generator 46 are connected together by means of the cable-handling device 20. The high voltage generator 46 and its load or X-ray tube 50 are connected together by means of the high voltage cable 48.

The DC source 70 and the primary winding 76 of a transformer 74 are connected together by means of a switching element 72, to which a diode 80 is connected in inverse parallel. A capacitor 82 is connected in parallel to the primary winding 76. The switching element 72, diode 80, capacitor 82 and primary winding 76 jointly constitute a voltage-resonance-type single-end switching circuit. This switching circuit, which is mainly voltage operated, offers the advantages that heat build up rarely occurs; the switch can be operated at a higher frequency for unit time; resonance can be effected at a high frequency on the order of several kHz units; and the transformer 74 can be provided by an air core transformer, thereby ensuring the miniaturization of a high voltage generator.

A secondary winding 78 of the transformer 74 consists of an n number of sections (78A1, 78A2, ... 78An). Thus a DC voltage supplied to the primary winding 76 is conducted to the secondary winding in the stepped-up form. A plurality of, for example, diode rectifiers (84A1, 84A2, ... 84An+1 and 84B1, 84B2, ... 84Bn+1) are connected to the secondary winding 78 to jointly constitute a rectifier circuit 84. The X-ray tube 50 is connected as a load to the output terminal of said rectifier circuit 84.

When insulated by oil, a high voltage generator 46 measuring 35 cm×35 cm×35 cm weighs about 60 kg. When insulated by gas, the generator 46 can have its weight reduced to about 30 kg. In other words, the generator 46 having a relatively small weight can be mounted on the support body 42 without obstructing the rotational balance of the rotating frame 40.

A description is now made of the structure of the cable-handling device 20 with reference to FIGS. 3 to 7. This cable-handling device 20 comprises a flat ring-shaped substrate 30 and a ring-shaped cable-holding housing 24 built on the substrate 30. The housing 24 is divided into an inner peripheral member 26 and an outer peripheral member 28, as radially viewed, which are slightly set apart from each other and respectively have a U-shaped cross section. A space is provided between the inner and outer peripheral members 26, 28 to permit the insertion of a plurality of rollers 32. The outer peripheral member 28 is fixed to the substrate 30, and the inner peripheral member 26 is held by a proper support (not shown) so as to be rotated concentrically with the outer peripheral member 28.

The shafts 33 of the plural rollers 32 are inserted between the edges of the inner peripheral member 26 and outer peripheral member 28 in parallel with the imaginary axis of the hole 22 of the cable-handling device 20.

A flat ring-shaped coupling member 34 is mounted on the peripheral member of the housing 24. The ring-shaped coupling member 34 comprises a plurality of (nine as indicated) holes 36. All the holes 36 except one are equidistantly arranged in the circumferential direction. The shafts 33 of the plural rollers 32 are inserted into the holes 36. According to the coupling member 34, the rollers 32 are arranged in the housing 24 at a prescribed distance in the circumferential direction. An auxiliary roller 39 is provided closely ahead of the specified roller 38 included in one group of rollers 32 as viewed from the direction of the arrow 4. The auxiliary roller 39 is rotatably received in the ring-shaped housing 24 like the other rollers 32.

Figure 5:
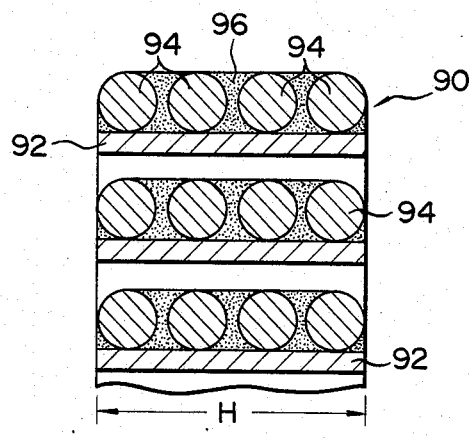
FIG. 5 is a cross sectional view of a cable member.

As shown in FIG. 5 cable member 90 comprises an elastic support strip 92 having a width H, and a plurality of cables 94 fixed to the support strip 92 by means of resin 96. A plurality of groups of four cables 94 are fixed to the support strip 92 in parallel. Any two of the four cables 94 constituting each group are used as power supply cables, and the other two are applied as signal cables. Resin 96 is filled in a space defined between the respective cables 94. The cables 94 are rendered bendable together with the support strip 92.

Figure 3:
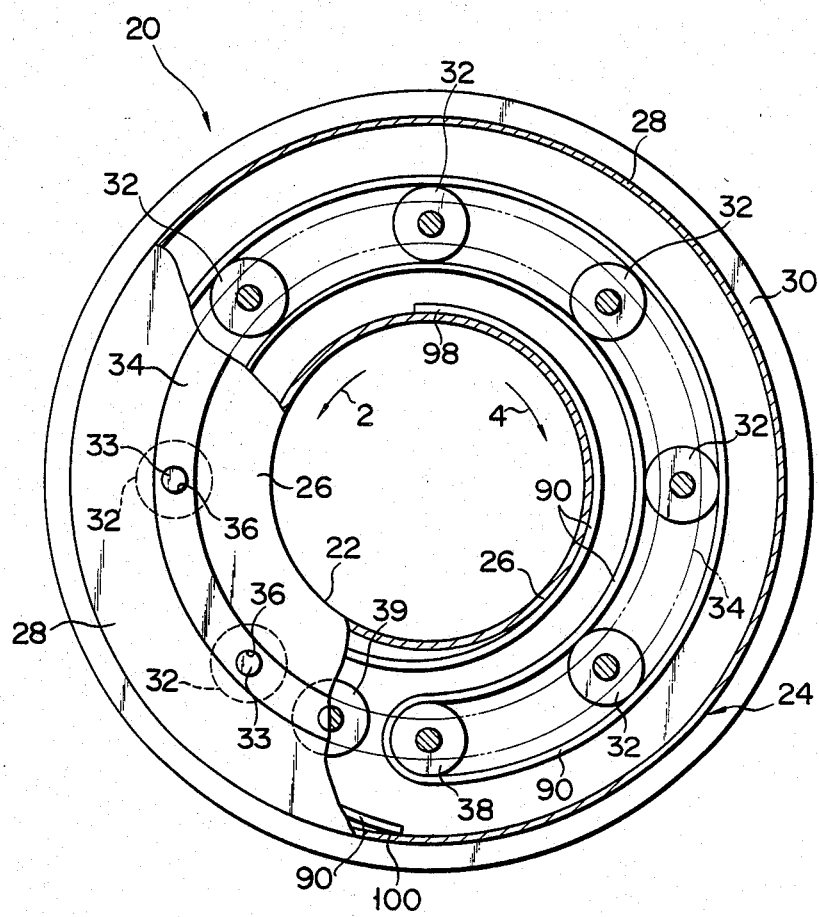
FIG. 3 is a sectional view of a plan indicating the interior of a cable-handling device.
Figure 4:
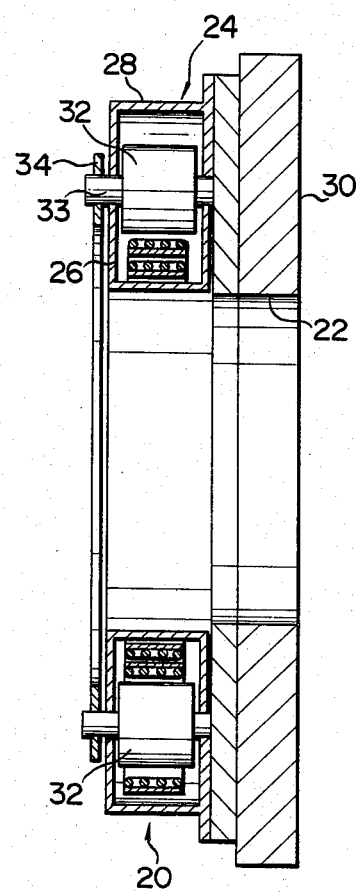
FIG. 4 is a cross sectional view showing the interior of the cable-handling device.

As illustrated in FIG. 3 the leading end 98 of that portion of the cable member 90 which is held in the housing 24 is fixed to the rotatable inner peripheral member 26. The cable member 90 is drawn out of the housing 24, starting with the leading end 98, to be connected to the high voltage generator 46 and power supply device 58 fixed to the support body 42. That portion of the cable member 90 which is held in the housing 24 is wound around the inner peripheral member 26 at least once (in FIG. 3, one and a half times clockwise, starting with the leading end 98). The cable member 90 is further wound about half the periphery of the specified roller 38 of the plural rollers 32 and then wound around the outside of the group of rollers 32 in a direction (counterclockwise) opposite to that in which the cable member 90 is wound around the inner peripheral member 26. After being wound several times around the outer periphery of the group of rollers 32, the cable member 90 is fixed to the outer peripheral member 28 at the rear end 100. The cable member 90 is drawn outside of the housing 24 at the rear end 100 to be connected to the DC source 70 (FIG. 2).

A description is now made of an X-ray CT scanner embodying this invention which is constructed as described above. The DC source 70 installed on the floor supplies DC voltage to the cable member 90 held in the cable-handling device 20 at the above-mentioned end 100. The DC voltage is impressed on the high voltage generator 46 and power source 58 at the leading end 98 of the cable member 90. A high voltage, stepped up by the high voltage generator 46, is supplied to the X-ray tube 50 by means of the high voltage cable 48, causing X-rays to be exposed from the X-ray tube 50. After being throttled by the iris diaphragm, the X-rays are irradiated on the patient held in the inserting hole 44. The X-rays permeating the patient are detected by the X-ray detector 54. The detected data are stored in the data acquisition system 56.

Figure 6:
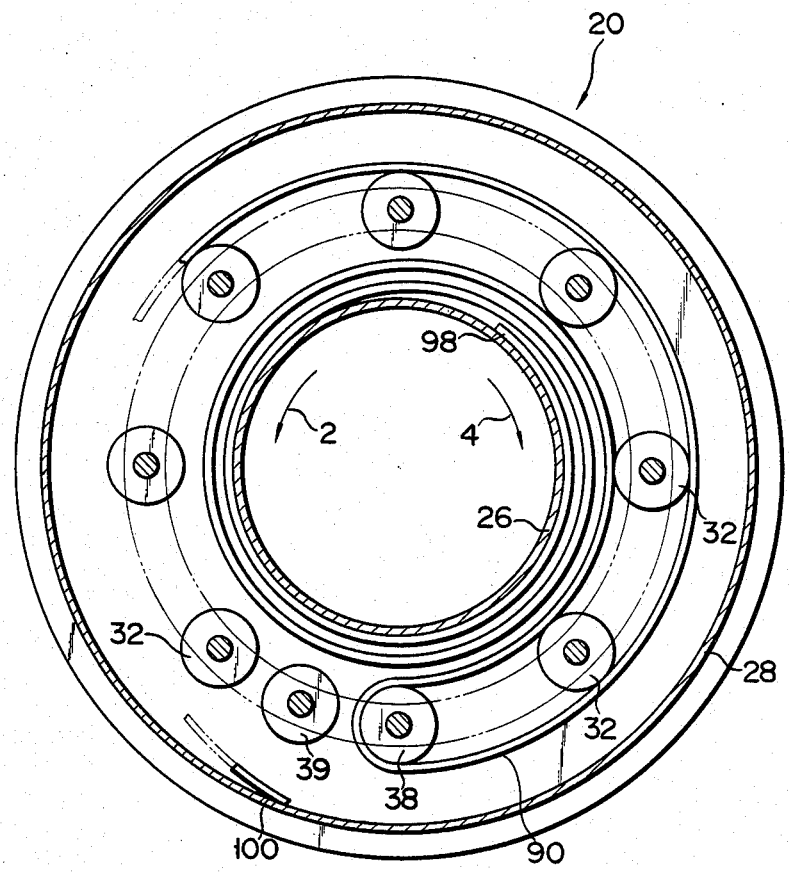
FIGS. 6 and 7 are sectional views of the plan illustrating the operation of the cable-handling device.

The data are collected while the rotating frame 40 is rotated. When the rotating frame 40 is rotated counterclockwise in the direction of an arrow 2 as shown in FIG. 6, the inner peripheral member 26 of the housing fixed to the leading end 98 of the cable member 90 is pulled thereby, or rotated together with the rotating frame 40, to be turned counterclockwise in the direction of the arrow 2. The counterclockwise rotation of the inner peripheral member 26 causes the cable member 90 held in the housing 24 to be pulled toward the inner peripheral member 26 by means of the leading end 98 of the cable member 90 and thus be wound around the inner peripheral member 26. As a result, the roller 38 wound with the cable member 90 is pulled counterclockwise in the direction of the arrow 2. Thus, the rollers 32 (including rollers 38, 39) are moved counterclockwise while being spaced from each other by the ring-shaped coupling member 34. The cable member 90 guided by the rollers 32 is prevented from being displaced from the regular course of rotation.

Figure 7:
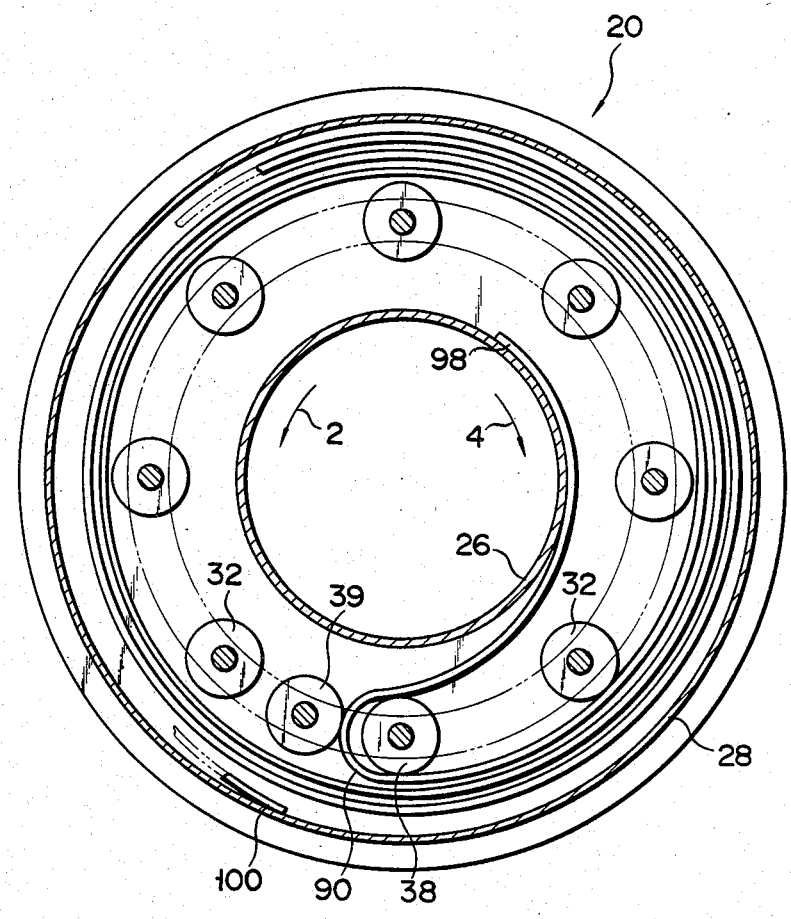

Later when the rotating frame 40 is turned clockwise in the direction of an arrow 4 shown in FIG. 7, the inner peripheral member 26 of the housing 24 is rotated in the same way. As a result, the cable member 90 wound around the inner peripheral member 26 is unwound therefrom. At this time, the support strip 92 of the cable member 90, which has a proper elasticity, is bent as shown in FIG. 7 when pressed against the roller 39 adjacent to the roller 38.

The auxillary roller 39 pushed by the cable member 90 is moved clockwise in the direction of the arrow 4 and, thus, the rollers 32 are also moved clockwise. Therefore, the cable member 90 guided by the rollers 32 is progressively wound around the outside of the group of rollers 32 along the inner plane of the outer peripheral member 28 of the housing 24 as shown in FIG. 7. A space defined between said auxiliary roller 39 and the specified roller 38 is made narrower than a space allowed between the respective rollers 32. Therefore, the cable member 90 unwound from the inner peripheral member 26 can be smoothly handled by the auxiliary roller 39.

When, therefore, the rotating frame 40 is rotated more than once as described above, the cable-handling device 20 can smoothly handle the cable member 90. In other words, the X-ray CT scanner of this invention enables the rotating frame 40 to be turned more than once without applying a slip ring as in the case of the conventional X-ray CT scanner. Since, with the X-ray CT scanner of this invention, the high voltage generator 46 is mounted on the support body 42 of the rotating frame 40, the high voltage cable 48 can be greatly shortened. Further, it is possible to provide a cable-handling device adapted for rotating the rotating frame 40 in the same direction with an optional frequency by adjusting the number of times by which the cable member 90 is wound in the housing 24.

What is claimed is:

1. A CT scanner for producing transverse layer images of a patient comprising:

a rotating frame having a hole which permits insertion of the patient, and which can rotate around the patient;

a stationary base for supporting the rotating frame;

a radiation source mounted on said rotating frame for exposing fan-shaped radiation beams on the patient;

a radiation detector set on the rotating frame for detecting the fan-shaped radiation beams permeating the patient;

a power source securely set at the sationary base for generating a first voltage power;

a high voltage generator built on the rotating frame for transforming a first voltage power to a second voltage power larger than the first voltage power and for impressing the second voltage power on the radiation source;

a cable member for conducting the first voltage power from the power source to the high voltage generator; and a cable-handling device for handling the cable member to permit the rotation of the rotating frame, the cable-handling device comprising a ring-shaped housing having an outer peripheral member and an inner peripheral member for holding the cable member wound between the outer peripheral member and the inner peripheral member, either of which is disposed on and rotatable with the rotating frame and the other of which is fixed at the stationery base; the cable-handling device also comprising a plurality of rollers each having a rotating shaft and being arranged in the housing in its circumferential direction, with the axis of the roller aligned with that of the housing, the cable member being wound around the inner peripheral member of the ring-shaped housing at least once in a first direction, wound about half the periphery of a prescribed one of the rollers, and wound at least once around the outside of the rollers in a second direction opposite to the first direction, and the end portions of the cable member facing the outer and inner peripheral members being fixed thereto; the cable-handling device further comprising a ring-shaped coupling member extending about the inner peripheral member of the ring-shaped housing, which is in engagement with the shafts of the rollers to position the rollers in the housing so as to surround the inner peripheral member, the ring-shaped coupling member being freely movable relative to the outer and inner peripheral members, and an auxiliary roller having a rotating shaft, arranged in the housing with the axis of the auxiliary roller aligned with that of the housing, and engaged with the ring-shaped coupling member, the auxiliary roller defining the locus of the cable member between the auxiliary roller and the prescribed one of the rollers.

2. The CT scanner according to claim 1, wherein the cable member comprises an elastic support strip and a cable fixed to the support strip.

3. The CT scanner according to claim 2, wherein said cable member comprises synthetic resin for fixing the cable to the support strip.

4. The CT scanner according to claim 3, wherein the cable member comprises a plurality of cables fixed in parallel to the support strip and synthetic resin filled in the interstices between the cables.

5. The CT scanner according to claim 1, wherein the outer and inner peripheral members of the ring-shaped housing are spaced from each other and the rotating shafts of the rollers are interposed between the outer and inner peripheral members of the ring-shaped housing.

6. The CT scanner according to claim 1, wherein the ring-shaped coupling member comprises a plurality of holes equidistantly arranged in the circumferential direction of the coupling member to permit the insertion of the shafts of the rollers for engagement.

7. The CT scanner according to claim 6, wherein the inner peripheral member of the ring-shaped housing is rotatable, and the outer peripheral member of said ring-shaped housing is fixed in place.

8. The CT scanner according to claim 1, wherein the high voltage generator is a voltage reasonance DC-DC converter-type.

* * * * *